(12) United States Patent
Arai

(10) Patent No.: US 11,445,894 B2
(45) Date of Patent: Sep. 20, 2022

(54) INSERTION ASSISTING SYSTEM

(71) Applicant: Olympus Corporation, Hachioji (JP)

(72) Inventor: Norimasa Arai, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 347 days.

(21) Appl. No.: 16/720,685

(22) Filed: Dec. 19, 2019

(65) Prior Publication Data

US 2020/0146538 A1 May 14, 2020

Related U.S. Application Data

(63) Continuation of application No. PCT/JP2017/024691, filed on Jul. 5, 2017.

(51) Int. Cl.
*A61B 1/00* (2006.01)
*A61B 1/233* (2006.01)

(52) U.S. Cl.
CPC ...... *A61B 1/00154* (2013.01); *A61B 1/00082* (2013.01); *A61B 1/00158* (2013.01); *A61B 1/233* (2013.01)

(58) Field of Classification Search
CPC ............ A61B 1/00082; A61B 1/00154; A61B 1/00158; A61B 1/233; A61B 1/00098; A61B 1/00177
See application file for complete search history.

(56) References Cited

U.S. PATENT DOCUMENTS 3,915,157 A * 10/1975 Mitsui ................ A61B 1/00165
600/107
3,924,608 A * 12/1975 Mitsui ................ A61B 1/00165
600/581
4,436,087 A * 3/1984 Ouchi ................ A61B 1/00165
600/153
(Continued)

FOREIGN PATENT DOCUMENTS

JP    H05-293106 A    11/1993
JP    H06-343597 A    12/1994
(Continued)

OTHER PUBLICATIONS

International Search Report dated Aug. 29, 2017 issued in International Application No. PCT/JP2017/024691.
(Continued)

*Primary Examiner* — Aaron B Fairchild
(74) *Attorney, Agent, or Firm* — Scully, Scott, Murphy & Presser, P.C.

(57) ABSTRACT

The disclosed technology is directed to an insertion assist system for an endoscope. The insertion assist system comprises a tube configured to control movement of an insertion portion of the endoscope during an advancing direction and a restrictor being disposed inside the tube and configured to restrict a protruding direction of the insertion portion. The tube includes an opening configured to receive the insertion portion to protrude therefrom. A guide surface is configured to control the advancing direction of the insertion portion and to restrict the protruding direction of the insertion portion. The restrictor is disposed facing the guide surface and is configured to press the insertion portion against the guide surface.

12 Claims, 4 Drawing Sheets

(56) References Cited

U.S. PATENT DOCUMENTS

| | | | | |
|---|---|---|---|---|
| 5,343,853 | A | * | 9/1994 | Komi .................... A61B 1/018 600/109 |
| 5,562,602 | A | * | 10/1996 | Yabe ........................ A61B 1/05 600/125 |
| 2001/0018550 | A1 | * | 8/2001 | Boebel ............... A61B 1/00098 600/114 |
| 2001/0044570 | A1 | * | 11/2001 | Ouchi ................ A61B 1/00177 600/107 |
| 2002/0091303 | A1 | * | 7/2002 | Ootawara ................ A61B 1/01 600/106 |
| 2005/0131278 | A1 | * | 6/2005 | Dickopp ............ A61B 1/00098 600/107 |
| 2006/0004323 | A1 | | 1/2006 | Chang et al. |
| 2007/0099500 | A1 | * | 5/2007 | Pilvisto .............. A61B 1/00098 439/584 |
| 2011/0071542 | A1 | | 3/2011 | Prisco et al. |

FOREIGN PATENT DOCUMENTS

| | | |
|---|---|---|
| JP | 2005-046277 A | 2/2005 |
| JP | 4959550 A | 6/2012 |
| JP | 2014-018563 A | 2/2014 |
| JP | 6000382 A | 9/2016 |

OTHER PUBLICATIONS

International Preliminary Report on Patentability dated Jan. 16, 2020 together with the Written Opinion received issued in International Application No. PCT/JP2017/024691.

* cited by examiner

INSERTION ASSISTING SYSTEM

CROSS-REFERENCE TO RELATED APPLICATION

This application is a continuation application of PCT Application No. PCT/JP2017/024346 filed on Jul. 3, 2017, which is hereby incorporated by reference in its entirety.

TECHNICAL FIELD

The disclosed technology relates to an insertion assist system for restricting a protruding direction of a soft insert object to be inserted into an observation target.

DESCRIPTION OF THE RELATED ART

An insertion portion of a flexible endoscope includes at a distal end portion thereof at least an illuminating window through which illuminating light is radiated, and an observation window or the like through which an optical image as an observation image is optically captured. As these windows are disposed, the distal end portion of the insertion portion is formed as a sheath member from a hard material, for example, a metal material. On the other hand, the insertion portion of the flexible endoscope, when bent, generally has resilience sufficient to return from a bent form to an original straight form.

As a flexible endoscope, there is an endoscope that is used to observe inside the paranasal sinuses. This paranasal sinus endoscope also includes at a distal end portion thereof a hard, distal end portion, i.e., a hard portion having a certain length or a hard length. The paranasal sinus endoscope is inserted at a distal end thereof from a sinus ostium, and the distal end portion is allowed to pass through a small-diameter opening in the nasal cavity and to reach a maxillary sinus. For example, the system proposed by the Japanese Patent No. 4958550 (PTL 1) uses a technique to insert a flexible endoscope into a sphenoid sinus to perform observation and treatment.

In the observation of the sphenoid sinus as described hereinbefore, the flexible endoscope can be inserted straight. On the other hand, the opening of each maxillary sinus or frontal sinus is located in a lateral side as viewed from the sinus ostium. When inserting the flexible endoscope from the opening of the maxillary sinus or frontal sinus, there is hence a need to arrange a desired means such as a guide member at the distal end portion of the flexible endoscope and to insert the distal end portion from the opening while bending an insertion portion. PTL 1 proposes a technique to widen the closed opening to a paranasal sinus with a catheter and then to insert the distal end portion.

If a pipe-shaped guide member having a curved portion is used as a bending guide member, i.e., a clearance, which corresponds to the hard length of the distal end portion and allows the distal end portion to advance around is needed to permit passage of the hard, distal end portion of the flexible endoscope to pass beyond the curved location.

For the additional inclusion of the clearance, this guide member increases in width, i.e., cross-sectional area in a vicinity of a curved guide surface configured to determine the advancing direction of the flexible endoscope, and has a drawn shape tapered toward a distal end opening of the guide member. Owing to the resilience that the insertion portion has, a force acts on the flexible endoscope to make it return to a straight shape in the clearance formed by the guide member, so that the insertion portion separates from a guide surface that is an inner wall surface of the guide member. As a consequence, the insertion portion of the flexible endoscope protrudes in an unintended direction.

BRIEF SUMMARY OF EMBODIMENTS

The disclosed technology is directed to an insertion assist system for an endoscope. The insertion assist system comprises a tube configured to control movement of an insertion portion of the endoscope during an advancing direction and a restrictor being disposed inside the tube and configured to restrict a protruding direction of the insertion portion. The tube includes an opening configured to receive the insertion portion to protrude therefrom. A guide surface is configured to control the advancing direction of the insertion portion and to restrict the protruding direction of the insertion portion. The restrictor is disposed facing the guide surface and is configured to press the insertion portion against the guide surface.

Another aspect of the disclosed technology is directed to a tubular insertion assist system capable of causing protrusion of an elongated insert object, which has a hard portion at a distal end thereof, from a distal end of the tubular insertion assist system. The tubular insertion assist system comprises a guide tube formed from a tube having an opening at a distal end thereof and a channel enabling insertion of the insert object therethrough and having a shape bent in a direction at a curved location and tapered toward the opening. A restrictor is disposed extending along the guide tube from the opening at the distal end to a proximal end of the guide tube. The tube includes a first curved portion having a predetermined curvature in a vicinity of the curved location and configured to enable formation of a clearance between the insert object and the tube when the distal end of the insert object has been inserted to the opening. A second curved portion having a curvature greater than the predetermined curvature so that the channel has a diameter greater than the opening. The restrictor is configured to be switchable between a first situation in which the restrictor is disposed extending along the first curved portion. A second situation in which the restrictor presses the insert object against an inner wall surface of the guide tube so that the insert object extends along and in parallel to the second curved portion.

A further aspect of the disclosed technology is directed to a method of operating an insertion assist system for an endoscope into an affected part, the method comprises directing an insertion portion of the endoscope to advance along a guide surface of a tube configured to control movement of the insertion portion during an advancing direction, restricting a path along which the insertion portion advances, by moving a restrictor, which is disposed facing the guide surface in a direction toward the guide surface and pressing the restrictor against the insertion portion, and resulting the endoscope to advance with the path remaining restricted, whereby the endoscope is caused to protrude in a predetermined direction from an opening of the tube.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

Embodiments of the disclosed technology will hereinafter be described in detail with reference to the drawings.

First Embodiment

An insertion assist system 2 according to a first embodiment will be described. A target of assistance by this insertion assist system 2 is an elongated flexible insert object, examples of which include endoscopes, catheter, guide wires and the like to be inserted into at least a body cavity or lumen. The term "elongated flexible" in the embodiments to be described hereinafter implies to have resilience or flexibility in the direction of a longitudinal axis, and may mean resilience or stiffness in a radial direction. At a distal end of the flexible insert object, a hard portion is arranged. The hard portion is formed from a hard member and has a desired length, i.e., a hard length. An endoscope includes in a hard portion thereof at least an illuminating window through which illuminating light is radiated, and an observation window or the like through which an optical image as an observation image is optically captured. Further, the target of assistance by the insertion assist system 2 in this embodiment may preferably be an instrument that does not include a bending mechanism which bends positively and is mounted in a distal end portion on an inserting side of the instrument.

In addition, the flexible insert object is suitably an instrument which when bent, has resilience, i.e., a restoring force sufficient to return from a bent form to a straight form of a certain extent. The term "resilience" in the embodiments to be described hereinafter means a property that is prone to moderate deformation upon application of a force and has good restorability from the deformation. Targets of assistance are not limited only to medical instruments and observation instruments for biological objects, but the insertion assist system 2 can be also applied easily to elongated observation instruments, which are to be inserted into piping structures formed from hard members or internal mechanisms of machines such as engines and include an imaging unit or the like and an observation window in distal ends thereof, or elongated members such as wires.

Figure 1:
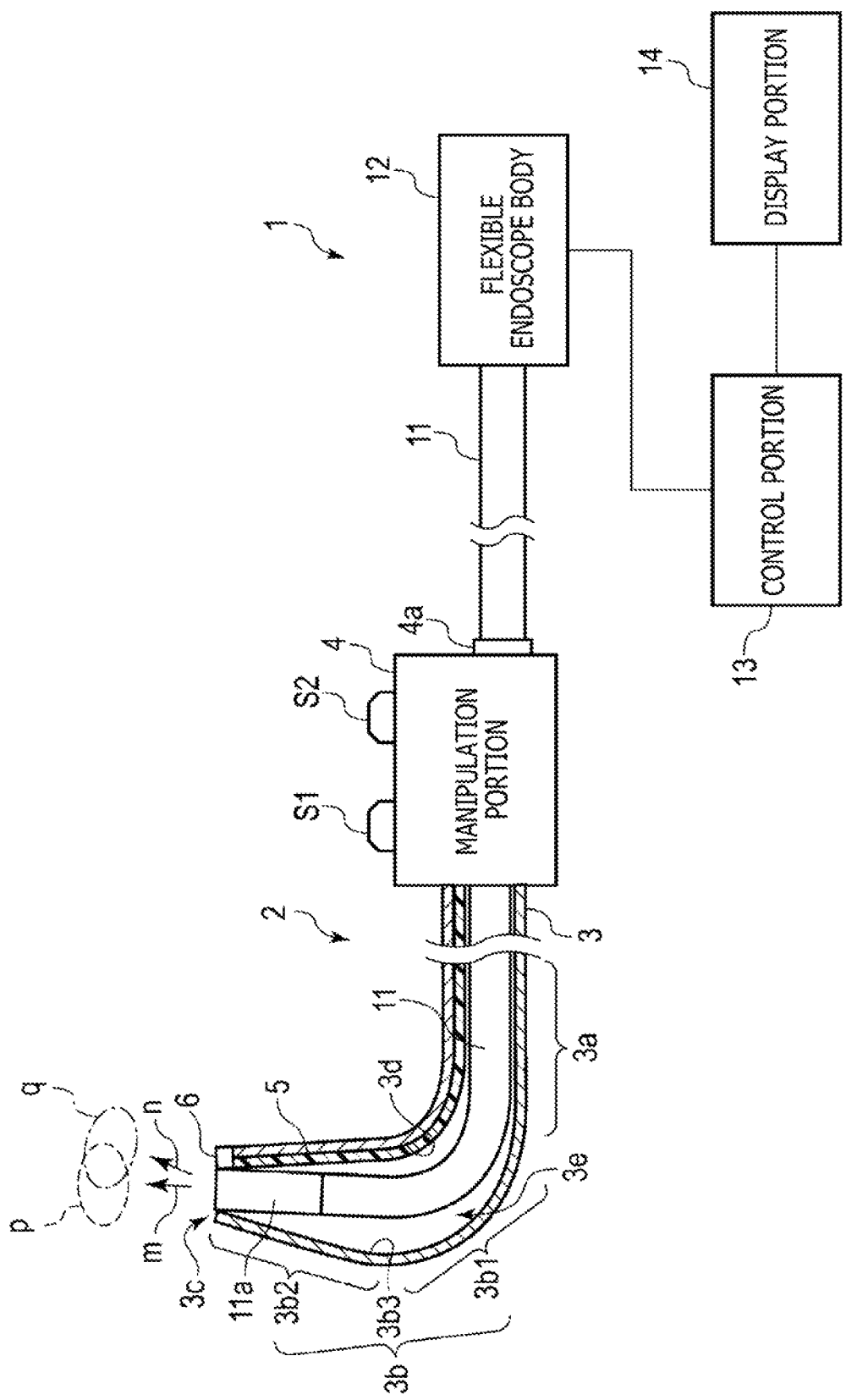
FIG. 1 is a view illustrating a concept configuration of an insertion assist system according to a first embodiment of the disclosed technology as applied to a flexible endoscope.
Figure 2A:
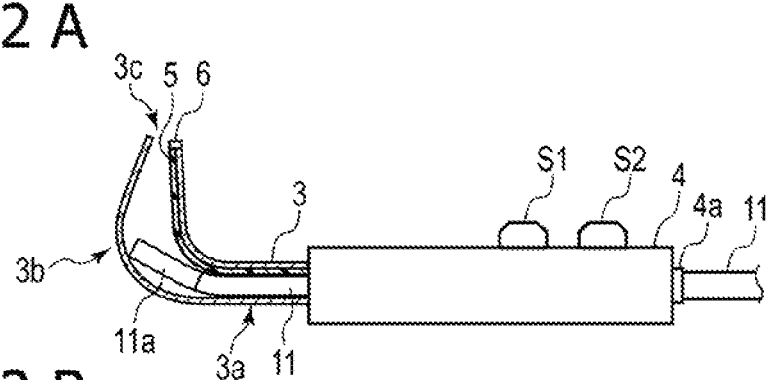
FIG. 2A is a view illustrating a situation in which an insertion portion of the flexible endoscope advances in the insertion assist system for a flexible insert object.
Figure 2B:
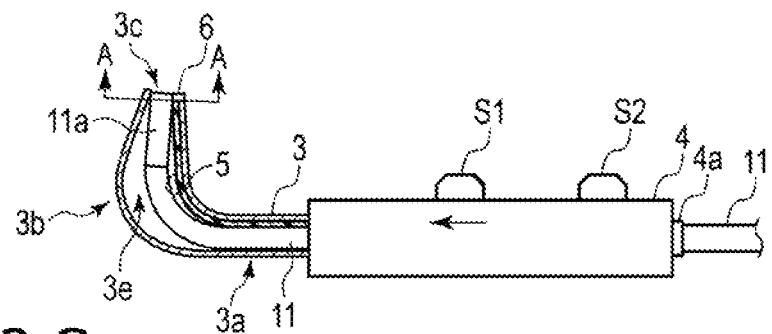
FIG. 2B is a view illustrating another situation in which the insertion portion of the flexible endoscope stops at a distal end of a guide tube in the insertion assist system.
Figure 2C:
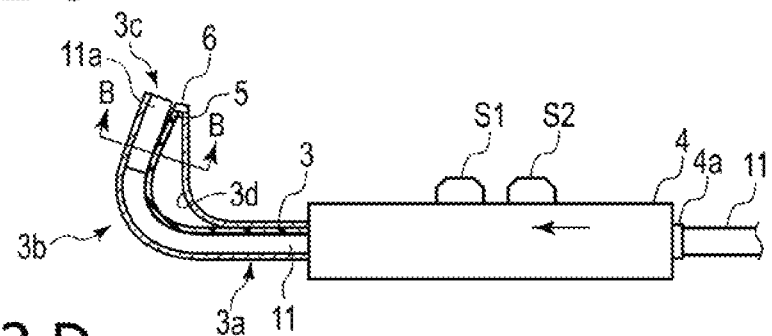
FIG. 2C is a view illustrating a further situation in which an insert-object restricting portion has separated out in the guide tube of the insertion assist system.
Figure 2D:
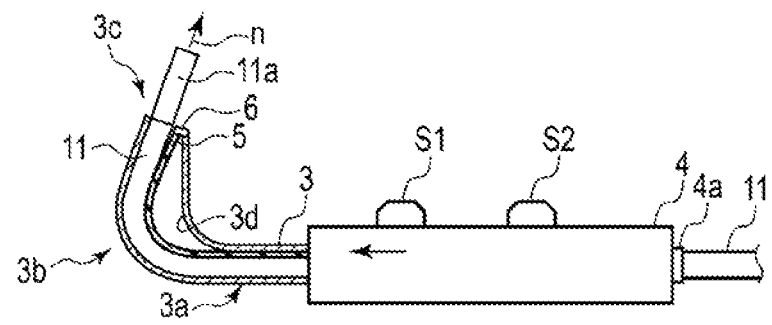
FIG. 2D is a view illustrating a yet further situation in which the insertion portion of the flexible endoscope has protruded, with its protruding direction restricted, from the distal end of the guide tube in the insertion assist system.
Figure 2E:
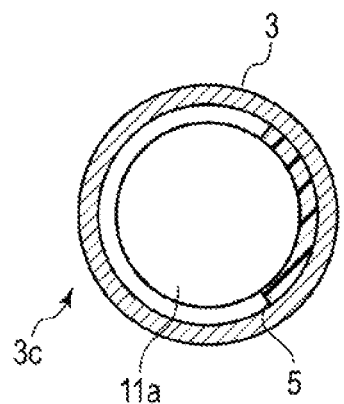
FIG. 2E is a cross-sectional view illustrating a cross-sectional shape of the insertion assist system along line A-A of FIG. 2B.
Figure 2F:
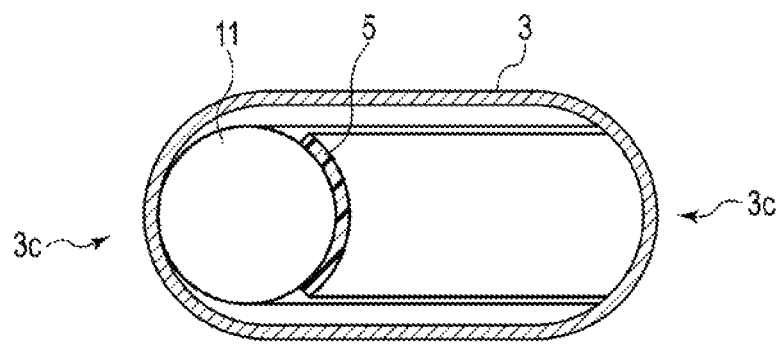
FIG. 2F is a cross-sectional view illustrating a cross-sectional shape of the insertion assist system along line B-B of FIG. 2C.

In this embodiment to be described hereinafter, a description will be made taking, as an example, a flexible endoscope 1 that a target of assistance by the insertion assist system 2 is inserted into a body cavity or a lumen. The flexible endoscope 1 has the resilience or restoring force described hereinbefore. The flexible endoscope 1 can be a paranasal sinus endoscope for observing the paranasal sinuses. FIG. 1 is a view illustrating a concept configuration of the insertion assist system 2 according to the first embodiment as applied to the flexible endoscope 1, FIG. 2A is a view illustrating a situation in which an insertion portion of the flexible endoscope 1 advances, FIG. 2B is a view illustrating another situation in which the insertion portion of the flexible endoscope 1 stops at a distal end of a guide tube 3, FIG. 2C is a view illustrating a further situation in which an insert-object restricting portion 5 has separated out in the guide tube 3, FIG. 2D is a view illustrating a yet further situation in which a flexible insertion portion 11 of the flexible endoscope 1 has protruded from the distal end of the guide tube 3, FIG. 2E is a cross-sectional view illustrating a cross-sectional shape of the insertion assist system 2 along line A-A of FIG. 2B, and FIG. 2F is a cross-sectional view illustrating a cross-sectional shape of the insertion assist system 2 along line B-B of FIG. 2C.

As illustrated in FIG. 1, the flexible endoscope 1 is configured of the flexible insertion portion 11, a flexible endoscope body 12 integrally connected with the insertion portion 11, a control portion 13 that performs control including image processing, and a display portion 14 that displays image information including a captured observation image.

The insertion portion 11 has in a distal end portion 11a thereof at least the illumination window, the observation window and the like as described hereinbefore. Because of a structure with the individual windows disposed therein, this distal end portion 11a, i.e., hard portion uses, as a sheath member, a cylindrical member formed from a hard material, for example, a metal material. Inside the insertion portion 11, at least a light guide and an optical fiber is arranged extending therethrough although they are not illustrated in the drawing. The light guide guides illuminating light, and the optical fiber transmits a captured optical image.

Inside the flexible endoscope body 12, an imaging portion (not illustrated) having an imaging device such as a concatenated disk driver or charge-coupled device (CCD) or a complementary metal-oxide semiconductor (CMOS) is arranged. The imaging portion forms an image based on the captured optical image propagated through the optical fiber, converts the image to video signals by photoelectric conversion, and delivers the video signals to the control portion 13. The control portion 13 applies various image processing to the video signals, and displays the resulting image on the display portion 14.

The insertion assist system 2 of this embodiment includes a guide 3, i.e., a tube, an insert-object restricting portion 5, i.e., a restrictor, and a manipulator 4. The guide 3, i.e., the tube allows insertion of the insertion portion 11 of the flexible endoscope 1 therealong, and has a guide surface 3$b$3 to be described hereinafter. The insert-object restricting portion 5, i.e., the restrictor is arranged in the guide tube 3 and has a band shape. The manipulator 4 performs a separate-out operation for the insert-object restricting portion 5 and a moving operation to push in or draw out the insertion portion 11. In the description to be made hereinafter, in the guide tube 3, a side on which an opening 3$c$, through which the flexible endoscope 1 protrudes, is arranged will be called "the distal end side," and a side, on which the guide tube 3 is connected to the manipulator 4, will be called "the proximal end side."

Using a metal material or a hard resin material, the guide tube 3 is formed as a substantially L-shaped pipe bent at a curved location thereof in a direction that intersects a longitudinal direction. The guide tube 3 is configured of a straight portion 3$a$ on the proximal end side and a guide portion 3$b$. The straight portion 3$a$ extends from the manipulator 4, and the guide portion 3$b$ includes a curved portion 3$b$1 on the distal end side of the straight portion 3$a$. As illustrated in FIG. 1, the straight portion 3$a$ of the guide tube 3 has a diameter, i.e., a size in cross-portion, which is sufficient to insert the insertion portion 11 of the flexible endoscope 1 as the target of assistance without resistance. It is to be noted that the cross-sectional shape and the size in cross-portion of the guide tube 3 are appropriately set based on the flexible insert object as the target of assistance. Further, the protruding direction which is restricted by the guide tube 3 is also appropriately set depending on the target of assistance and the target of observation. In the case of a flexible endoscope that is used to observe the maxillary sinuses of the paranasal sinuses, for example, the protruding direction may preferably be curved at approximately 110° with respect to the longitudinal direction of the guide tube 3.

To allow the hard, distal end portion 11$a$ of the insertion portion 11 to advance around the curved location upon passing beyond the curved location, the guide portion 3$b$ needs a clearance 3$e$ as described hereinbefore. In a transverse cross-sectional plane as illustrated in FIG. 2F, the clearance 3$e$ is formed in an elongated hole shape that is widened toward the distal end side in the longitudinal direction of the guide tube 3 according to the length of the hard distal end portion 11$a$, in other words, the length of the hard portion, i.e., the hard length of the insertion portion 11. Because of the arrangement of the clearance 3$e$, the guide portion 3$b$ is formed in a bottle shape of a small thickness in a vertical direction, which has a drawn shape tapered toward the circular opening 3$c$ at the distal end as illustrated in FIG. 2E.

This guide portion 3$b$ is formed of a curved portion 3$b$1, i.e., a second curved portion and a straight portion, i.e., a protruding-direction restricting portion 3$b$2. The curved portion 3$b$1, i.e., the second curved portion includes the clearance 3$e$, and allows the insertion portion 11 to advance around in the direction in which the insertion portion 11 is caused to protrude. The straight portion, i.e., the protruding-direction restricting portion 3$b$2 is formed in a drawn shape tapered straight from the curved portion 3$b$1 to the opening 3$c$. The straight portion 3$b$2 is formed to have a length, i.e., a hard length over which at least the hard portion, which is the distal end portion 11$a$ of the insertion portion 11, can be applied. This length ensures the boundary between the hard, distal end portion 11$a$ and the flexible portion of the insertion portion not to come to the curved portion 3$b$1, thereby preventing application of a load to the boundary during restriction by the insert-object restricting portion 5. In this example, the boundary between the hard distal end portion 11$a$ and the flexible portion of the insertion portion is set to come into contact with the straight portion 3$b$2 by making the distal end of the distal end portion 11$a$ of the insertion portion 11 flush with the distal end of the opening 3$c$ of the guide tube 3.

In an inner surface of the guide portion 3$b$, a surface with which the insertion portion 11 pushed by the insert-object restricting portion 5 comes into contact and which determines the protruding direction of the insertion portion 11 will be referred to as the guide surface 3$b$3. Described specifically, the guide surface 3$b$3 is an inner surface on the distal end side in the curved portion 3$b$1 and straight portion 3$b$2. In this embodiment, an inner surface or the proximal end side of the guide portion 3$b$, the inner surface, i.e., the proximal end side facing the guide surface 3$b$3, is arranged as a restricting-member receiving surface 3$d$, i.e., a first curved portion, which is in the form of a straight semi-cylindrical surface and on which the insert-object restricting portion 5 is received so as to be held in close contact therewith. It is to be noted that the curved portion 3$b$1 is formed to have a greater curvature than the predetermined curvature at the restricting-member receiving surface 3$d$.

The insert-object restricting portion 5 is a member, which is a metal sheet or resin plate in the form of a band shape, forms a curved surface of a curvature equivalent to the inner diameter of the guide tube 3 or a planar surface, and has flexibility and resilience. The insert-object restricting portion 5 is disposed so as to extend through the guide tube 3, and as illustrated in FIGS. 1 and 2E, is openably and closably fixed at an end thereof by a fixing portion 6 on the opening 3$c$ of the guide tube 3 on the side of the restricting-member receiving surface 3$d$. Further, the insert-object restricting portion 5 extends through the guide tube 3, and is connected at an opposite end thereof to a restrictor manipulator S2 at the manipulator 4. The restrictor manipulator S2 will be described hereinafter. By slidingly operating the restrictor manipulator S2 at the manipulator 4 as will be described hereinafter, the insert-object restricting portion 5 separates from the restricting-member receiving surface 3$d$ and moves to come out toward the distal end side as illustrated in FIG. 2C.

The manipulator 4 includes a housing formed, for example, in a cylindrical shape. This housing is not limited to the cylindrical shape insofar as it has a shape that facilitates the grasping by an operator. For example, a plurality of recesses may be arranged as finger rests on a surface located on a side opposite to the manipulators to be described subsequently hereinafter. The guide tube 3 is arranged on a distal end side of the housing of the manipulator 4, and an inlet 4$a$ is arranged on a proximal end side of the housing. The inlet 4$a$ is used to draw a flexible insert object such as the insertion portion 11 of the flexible endoscope 1 into the housing.

The manipulator 4 also includes an insertion portion manipulator S1 and a restricting portion manipulator S2. The insertion portion manipulator S1 is disposed on a side, i.e., a forward side on which the guide tube 3 extends, and is used to perform moving operations such as push-in and draw-out of the insertion portion 11, and the restricting portion manipulator S2 is disposed on a rear side and is used to perform a separate-out operation of the insert-object restricting portion 5. The insertion portion manipulator S1 and restricting portion manipulator S2 in this embodiment perform operations by slidingly moving back and force in the longitudinal direction along the guide tube 3. The insertion portion manipulator S1 includes an unillustrated clamping mechanism in the manipulator 4, and causes the clamping mechanism to clamp the insertion portion 11 or to release the clamping. The clamping mechanism may have a general simple configuration, for example, a configuration that two arms, which extend facing each other, are biased to come toward each other by elastic members. The insertion portion 11 is clamped between these arms, and is maintained in the clamped state under elastic forces. The insertion portion manipulator S1 is slidingly moved to perform push-in and draw-out movements of the clamped insertion portion 11.

Referring to FIGS. 2A to 2D, a description will be made about push-in and draw-out out movements of the insertion portion 11 by operations at the manipulator 4 and the restriction to the protruding direction of the insertion portion 11 by the insert-object restricting portion 5.

First, as illustrated in FIG. 2A, the insertion portion 11 of the flexible endoscope 1 is inserted from the inlet 4a arranged on a proximal end side of the manipulator 4. By the operator's inserting action, the insertion portion 11 is caused to pass through the insides of the manipulator 4 and guide tube 3, and is guided to the unillustrated clamping mechanism of the insertion portion manipulator S1. The insertion portion 11 is pushed forward further, and as illustrated in FIG. 2A is brought at the distal end portion 11a thereof into contact with the guide surface 3b3. It is to be noted that after reaching the clamping mechanism, the insertion portion 11 may be clamped by an operation of the insertion portion manipulator S1 and may then be pushed forward in the guide tube 3 to come into contact with the guide surface 3b3.

After the distal end portion 11a of the insertion portion 11 has come into contact with the guide surface 3b3, the insertion portion 11 is clamped by an operation of the insertion portion manipulator S1, and is pushed forward in the guide tube 3 while being maintained at the distal end portion 11a thereof in contact with the guide surface 3b3. When the distal end of the distal end portion 11a has reached the distal end of the opening 3c of the guide tube 3 as illustrated in FIG. 2B, i.e., in a first situation, the push-in operation for the insertion portion 11 is stopped.

When the restricting portion manipulator S2 at the manipulator 4 is next operated slidingly, the insert-object restricting portion 5 is pushed to separate out from the straight portion 3a of the guide tube 3. As illustrated in FIG. 2C, i.e., a second situation, the insert-object restricting portion 5 then separates from the restricting-member receiving surface 3d, with the fixing portion 6 acting as a fulcrum, while maintaining a curved shape. As a consequence, the insert-object restricting portion 5, as a whole, comes into contact with the insertion portion 11 so that the insertion portion 11 is pushed toward the guide surface 3b3 to extend along the guide surface 3b3. Owing to this contact by the insert-object restricting portion 5, the protruding direction of the insertion portion 11 of the flexible endoscope 1 is restricted to lie in parallel to the longitudinal direction of the guide surface 3b3.

As illustrated in FIG. 2D, by a subsequent operation of the insertion portion manipulator S1 at the manipulator 4, the insertion portion 11 clamped by the unillustrated clamping mechanism is pushed forward in the guide tube 3, and is caused to protrude from the opening 3c of the guide tube 3 in a direction n restricted to the longitudinal direction of the guide surface 3b3 by the insert-object restricting portion 5.

With reference to FIG. 1, a description will next be made about operations and advantageous effects of the insert-object restricting portion 5 in the insertion assist system 2 of this embodiment.

In this embodiment, the guide tube 3 includes the clearance 3e which is needed to change the advancing direction of the hard, distal end portion 11a of the insertion portion 11. As illustrated in FIG. 1, the insert-object restricting portion 5 is received so as to be brought into contact with the restricting-member receiving surface 3d, and, in a state that no restriction assistance exists to the protruding direction, the position of the distal end portion 11a of the insertion portion 11 is determined by the opening 3c of the guide tube 3. However, the flexible portion of the insertion portion 11, which continues to the distal end portion 11a, tends to return into the original straight form by its resilience so that in the clearance 3e, the flexible portion comes into a state in which it is apart from the guide surface 3b3. In such a state, even if the insertion portion 11 is paid out further by an operation at the manipulator 4 in an attempt to bring the insertion portion 11 into contact with the guide surface 3b3, the insertion portion 11 once moves toward the guide surface 3b3 but returns to the original position by the resilience. For a backlash of the return movement, the distal end portion 11a is consequently caused to protrude in an unexpected direction from the opening 3c of the guide tube 3 as will be described hereinafter.

By the guide surface 3b3 of the guide tube 3, the protruding direction of the insertion portion 11 should be restricted to a direction that is parallel to the longitudinal direction of the guide surface 3b3. In FIG. 1, the insertion portion 11 is set to protrude in the direction of the protruding direction n. If desired to pass through an opening q in a nasal cavity, for example, the positioning of the insertion assist system 2 is supposed to be conducted so that the opening q lies ahead in the protruding direction n. As described hereinbefore, however, the insertion portion 11 has an inclination, i.e., posture affected by its resilience in the clearance 3e. If the insertion portion 11 is paid out by an operation at the manipulator 4 in FIG. 1, the insertion portion 11 hence actually protrudes in the direction m of the central axis of a portion of the insertion portion 11, where the insertion portion 11 is in a straight form. If the opening q does not lie ahead, the insertion portion 11 is not inserted into the opening q accordingly. As appreciated from the foregoing, the insertion portion 11 protrudes to a position p deviated from a position perceived by the operator. Especially depending on the difference in the magnitude of resilience, the posture, i.e., the degree of inclination of the insertion portion 11 in the clearance 3e differs, and so the protruding direction. It is therefore difficult to predict the protruding direction. The foregoing hence suggests the difficulty of disposing the insertion assist system 2 at a position where the insertion portion 11 of the flexible endoscope 1 can be inserted into an opening of an observation target.

To lessen or overcome the difficulty described hereinbefore, this embodiment, as illustrated in FIG. 2C, causes the insert-object restricting portion 5 to separate out so that the insertion portion 11 is applied to the guide surface 3b3 to restrict the protruding direction of the insertion portion 11. As a consequence, the insertion portion 11 is protruded to a position perceived by the operator, and therefore the positioning of the insertion assist system 2 can be conducted toward an opening of an observation target, for example, an opening of a paranasal sinus without confusion.

Further, the insert-object restricting portion 5 is a planar sheet in the form of a band disposed in the longitudinal direction, and is received so that it is in contact with the inner wall surface of the straight portion 3a of the guide tube 3. Even if the moving insertion portion 11 comes into contact with the insert-object restricting portion 5, a push-in or draw-out movement of the insertion portion 11 is not interfered accordingly. The insert-object restricting portion 5 has flexibility and resilience, and comes into contact with the insertion portion 11 or the flexible insert object so that the insert-object restricting portion 5 is applied at a planar concave curved surface thereof to the outer circumferential wall of the insertion portion 11, i.e., the flexible insert object. The insert-object restricting portion 5 therefore does not give damage such as scratches to the outer circumferential surface of the insertion portion 11.

In this embodiment, the insert-object restricting portion 5 is separated out until the insertion portion 11 comes into contact with the guide surface 3b3. It is, however, possible to adjust the protruding direction at a desired angle smaller than that of the protruding direction, which is restricted by the guide surface 3b3, by stopping the insertion portion 11 at a desired position before it comes into contact with the guide surface 3b3. The insertion assist system 2 of this embodiment has a mechanism that pushes the insert-object restricting portion 5 toward the guide surface 3b3 from one side. Therefore, the opening 3c of the guide tube 3 can maintain its precise shape so that the insertion performance of the insertion assist system 2 to the location of an observation target is not impaired.

Second Embodiment

Figure 3A:
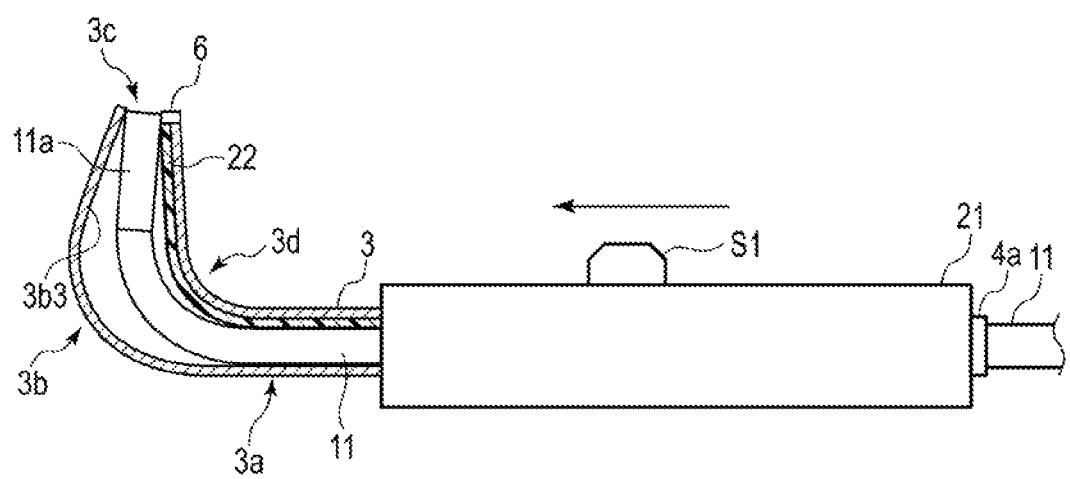
FIG. 3A is a view illustrating a configuration of an insertion assist system according to a second embodiment as applied to a flexible endoscope.
Figure 3B:
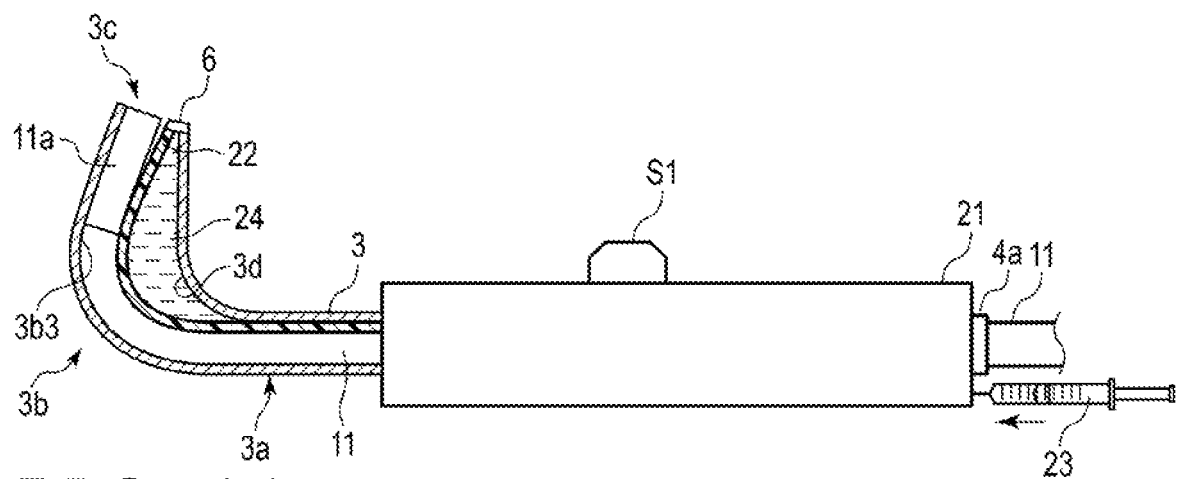
FIG. 3B is a view illustrating a situation in which an insert-object restricting portion has swollen in a guide portion of the insertion assist system.

Referring to FIGS. 3A and 3B, a description will next be made about an insertion assist system 2 according to a second embodiment. The insertion assist system 2 is for application to a flexible insert object. FIG. 3A is a view illustrating a concept configuration of the insertion assist system 2 according to the second embodiment, and FIG. 3B is a view illustrating a situation in which the protruding direction is restricted by the insertion assist system 2. Concerning elements of structure in the second embodiment, those which are equivalent to the corresponding ones in the first embodiment described hereinbefore are identified by like reference signs, and their description is omitted.

In this embodiment, as an insert-object restricting portion 22, a stretchable elastomer such as rubber is formed into a band-shaped film. The insert-object restricting portion 22 is fixed on the inner wall surface of the guide tube 3, i.e., the restricting-member receiving surface 3d by bonding the insert-object restricting portion 22 water tight at a distal end of the band shape thereof to the fixing portion 6. The insert-object restricting portion 22 is also bonded water tight at opposite side portions of the band shape thereof to the straight portion 3a of the guide tube 3 until the manipulator 4 is reached. In the manipulator 4, an unillustrated pipe or tube is laid extending back and forth, and the insert-object restricting portion 22 is fixed water tight at a proximal end of the band shape thereof to the side of a proximal end of the pipe or tube. The pipe or tube is exposed at a proximal end thereof to an outside of the manipulator 4 so that the proximal end of the pipe or tube is arranged as an unillustrated injection port. Here, the pipe is assumed to be formed from a metal material or a hard resin material, while the tube is assumed to be formed from a soft resin material having flexibility. Their cross-sectional shapes may be selectively determined as desired.

When a syringe 23 is inserted into this injection port and a plunger is driven to inject a liquid 24, the liquid 24 flows through the pipe or tube and reaches the insert-object restricting portion 22. Further, the liquid 24 enters between the inner wall surface of the guide tube 3 and the insert-object restricting portion 22, and as illustrated in FIG. 3B, the insert-object restricting portion 22 swells into a balloon shape. The insert-object restricting portion 22 swollen into the balloon shape comes into contact, as a whole, with the insertion portion 11 so that the insertion portion 11 is pushed toward the guide surface 3b3 to extend along the guide surface 3b3. Owing to this contact by the insert-object restricting portion 5, the protruding direction of the insertion portion 11 of the flexible endoscope 1 is restricted to lie in parallel to the longitudinal direction of the guide surface 3b3.

By pulling the plunger of the syringe 23 backward, on the other hand, the liquid inside the insert-object restricting portion 22 is recovered into the syringe 23. In association with the recovery of the liquid, the swollen insert-object restricting portion 22 shrinks and comes into close contact with the inner wall surface of the guide tube 3. At this time, the elastic force of the insert-object restricting portion 22 contributes to the discharge of the liquid 24 by the shrinkage. This embodiment is configured to use the syringe, but may be configured to perform the injection and recovery of a liquid by using an electric pump. The injectable material to the insert-object restricting portion 22 is not limited to a liquid, but may be a certain fluid, for example, gas such as air, or microparticles formed from a metal material or resin material.

As a modification, the insert-object restricting portion 22 illustrated in FIG. 3B may be swollen with a fluid formed of a magnetic fluid instead of the liquid 24. By the magnetic force of the magnetic fluid, the hard portion of the distal end portion 11a of the insertion portion 11, the hard portion being optionally made from a metal, may be attracted and fixed on the opening 3c of the guide tube 3. A description will be made taking an example in which the distal end portion 11a of the insertion portion 11 is inserted into an opening at a location bent from an inserting direction, for example, to observe a paranasal sinus by the flexible endoscope 1.

Upon bringing the opening 3c of the guide tube 3 close to the opening of the paranasal sinus, the insertion portion 11 is inserted while rotating the insertion assist system 2 in various directions. A deviation is, therefore, expected to occur in the position of the distal end portion 11a relative to the opening 3c of the guide tube 3 as set before the insertion. If a positional deviation occurs and the distal end portion 11a of the insertion portion 11 is pulled back into the opening 3c, for example, the inside of the opening 3c is reflected to an image captured by the distal end portion 11a so that the observation field of vision is narrowed. It is therefore necessary to push the insertion portion 11 again into the guide tube 3 to conduct a positional adjustment. Here, the use of the magnetic fluid brings about an advantageous effect that a positional deviation hardly occurs, because the distal end portion 11 is attracted and fixed to the opening 3c by a magnetic force. However, the magnetic force of the magnetic fluid should be set to a strength in a range in which the insertion portion 11 can be moved by an operation of the insertion portion manipulator S1.

In this embodiment, an unillustrated clamping mechanism is also arranged in the manipulator 4 to clamp the insertion portion 11. The insertion portion 11 can be caused to protrude a desired length from the opening 3c of the guide tube 3 by clamping the insertion portion 11 through an operation of the insertion portion manipulator S1 and pushing the insertion portion 11 forward in the guide tube 3. Similarly, the protruded insertion portion 11 can be pulled back into the opening 3c of the guide tube 3, with the insertion portion 11 clamped, by an operation of the insertion portion manipulator S1.

In this embodiment described hereinbefore, equivalent advantageous effects can be brought about as in the first embodiment described hereinbefore. In addition, the insert-object restricting portion 22 in this embodiment brings the insertion portion 11 of the flexible endoscope 1 into contact with the guide surface 3b3 of the guide tube 3 by the swelling caused with the injected liquid, i.e., fluid. The insert-object restricting portion 22 therefore comes into contact with the contact surface on the side of the insertion portion 11 under uniform pressure even if the contact surface is rugged. As a consequence, the insertion portion 11 can be brought into contact with the guide surface 3b3 of the guide tube 3 under distributed pressure without concentration of a load at the boundary between the hard, distal end portion 11a of the insertion portion 11 and the flexible insertion portion continuing to the distal end portion 11a.

Third Embodiment

Figure 4A:
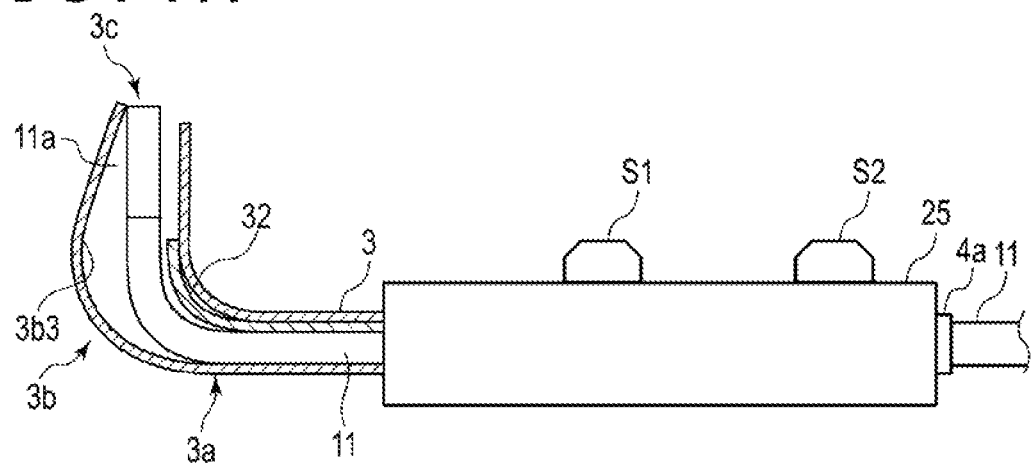
FIG. 4A is a view illustrating a configuration of an insertion assist system according to a third embodiment as applied to a flexible endoscope.
Figure 4B:
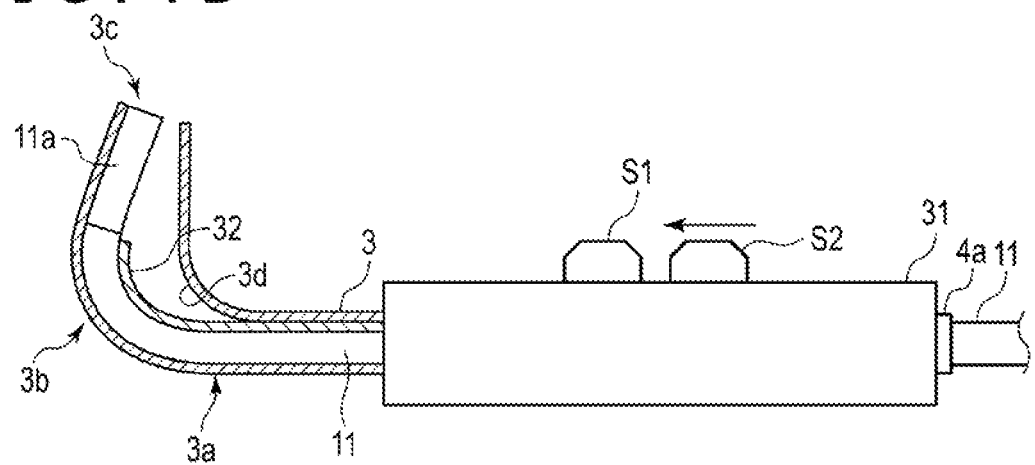
FIG. 4B is a view illustrating a situation in which an insert-object restricting portion has separated out in a guide portion of the insertion assist system.

Referring to FIGS. 4A and 4B, a description will next be made about an insertion assist system 2 according to a third embodiment. The insertion assist system 2 is for application to a flexible insert object. FIG. 4A is a view illustrating a concept configuration of the insertion assist system 2 according to the third embodiment, and FIG. 4B is a view illustrating a situation in which the protruding direction is restricted by the insertion assist system 2. Concerning elements of structure in the third embodiment, those which are equivalent to the corresponding ones in the first embodiment described hereinbefore are identified by like reference signs, and their description is omitted.

In this embodiment, a movable guide is used as an insert-object restricting portion 32, which is formed in a band shape from a metal material or a hard resin material and slidingly moves in the straight portion 3a of the guide tube 3.

As illustrated in FIG. 4A, the insert-object restricting portion 32 is formed in a curved shape by bending its distal end portion backward so that the distal end portion extends along the curved shape of the curved portion 3b1 (see FIG. 1) of the guide portion 3b. This insert-object restricting portion 32 extends on the side of a proximal end thereof through the straight portion 3a of the guide tube 3, and is connected there to the restrictor manipulator S2 at the manipulator 4.

The distal end portion of the insert-object restricting portion 32 has a height conforming to the curved portion 3b1 so that neither damage nor forcible bending occurs at at least the insertion portion 11. Desirably, the height of the distal end portion of the insert-object restricting portion 32 is set so that the distal end portion of the insert-object restricting portion 32 reaches around the center of the curved portion 3b1, where the arc of curving becomes deepest, and the flexible portion of the insertion portion 11, the flexible portion being on the side of the distal end of the hard distal end portion 11, is brought into contact with the guide surface 3b3 to avoid floating.

As illustrated in FIG. 4B, the restricting portion manipulator S2 is slidingly operated to push the insertion portion 11 of the flexible endoscope 1 toward the guide surface 3b3 by the insert-object restricting portion 32, whereby the insertion portion 11 is brought into contact with the guide surface 3b3 by the distal end portion of the insert-object restricting portion 32. By determining the slidable range of the restricting portion manipulator S2 beforehand, even if a distal end portion of the restricting portion manipulator S2 is moved to the most distal end at this time, the insertion portion 11 of the flexible endoscope 1 comes into contact at a side wall thereof with the guide surface 3b3 but stops before an overload or stress is exerted on the insertion portion 11. The distal end portion of the insert-object restricting portion 32 may be formed in a plate shape from an elastically deformable material such as, for example, a resin material. If the pressing against the outer circumferential surface of the insertion portion 11 by the distal end portion of the insert-object restricting portion 32 results in an overload, the distal end portion of the insert-object restricting portion 32 undergoes an elastic deformation so that the load can be released to prevent stress to the insertion portion 11. In this embodiment, an unillustrated clamping mechanism is also arranged in the manipulator 4 to clamp the insertion portion 11. The insertion portion 11 can be caused to protrude a desired length from the opening 3c of the guide tube 3 by clamping the insertion portion 11 through an operation of the insertion portion manipulator S1 and pushing the insertion portion 11 forward in the guide tube 3. Similarly, the protruded insertion portion 11 can be pulled back into the opening 3c of the guide tube 3, with the insertion portion 11 clamped, by an operation of the insertion portion manipulator S1.

In this embodiment described hereinbefore, equivalent advantageous effects can be brought about as in the first embodiment described hereinbefore. In addition, this embodiment is simpler in configuration than the first and second embodiments described hereinbefore. Moreover, the insert-object restricting portion 32 of the insertion assist system 2 of this embodiment can also adjust the protruding direction at a desired angle smaller than that of the protruding direction, which is restricted by the guide surface 3b3, by pushing the insertion portion 11 of the flexible endoscope 1 toward the guide surface 3b3 and then stopping the insertion portion 11 of the soft endoscope 1 at a desired position before it comes into contact with the guide surface 3b3.

The individual embodiments of the disclosed technology, which have been described hereinbefore, can create various inventions through appropriate combinations of plural elements disclosed herein. For example, some element or elements may be omitted from all the elements described in the embodiments. Furthermore, certain elements in different embodiments may be appropriately combined together.

In sum, the disclosed technology is directed to an insertion assist system for an endoscope. The insertion assist system comprises a tube configured to control movement of an insertion portion of the endoscope during an advancing direction and a restrictor being disposed inside the tube and configured to restrict a protruding direction of the insertion portion. The tube includes an opening configured to receive the insertion portion to protrude therefrom. A guide surface is configured to control the advancing direction of the insertion portion and to restrict the protruding direction of the insertion portion. The restrictor is disposed facing the guide surface and is configured to press the insertion portion against the guide surface.

The insertion assist system further comprises a manipulator being connected to an end of the tube. The manipulator is defined by a first manipulator configured to move the insertion portion back and forth in the tube and to cause protrusion of the insertion portion from the opening at an opposite end of the tube and a second manipulator configured to move the restrictor toward the guide surface. The restrictor has a band shape and flexible and is disposed extending through the tube. The restrictor at one end thereof is attached to the opening of the tube with the opening being to be used as a fulcrum and is connected at an opposite end thereof to the second manipulator. The restrictor is configured to be separated out toward a clearance by an operation of the second manipulator so that the insertion portion extends along the guide surface. The restrictor has a band shape and is formed from a flexible and resilience material. The restrictor is disposed extending through the tube and is attached at a circumferential edge thereof in close contact and being water tight with the tube.

The restrictor is configured to swell toward the clearance so that the insertion portion extends along the guide surface when a fluid is injected between a longitudinally central, non-close-contact portion of the restrictor and an opposite inner surface of the tube. The restrictor is formed from a band-shaped hard member having a distal end portion of a curve shaped that conforms to a curved portion of the guide surface. The hard member is disposed extending through the tube. The hard member is connected at a proximal end thereof to the second manipulator. The restrictor is configured to move toward the clearance by an operation of the second manipulator so that the distal end portion of the hard member is pressed against the insertion portion and the insertion portion extends along guide surface. The insertion portion is defined by an insertion portion of a flexible endoscope for paranasal sinus and a catheter and a guide wire.

Another aspect of the disclosed technology is directed to a tubular insertion assist system capable of causing protrusion of an elongated insert object, which has a hard portion at a distal end thereof, from a distal end of the tubular insertion assist system. The tubular insertion assist system comprises a guide tube formed from a tube having an opening at a distal end thereof and a channel enabling insertion of the insert object therethrough and having a shape bent in a direction at a curved location and tapered toward the opening. A restrictor is disposed extending along the guide tube from the opening at the distal end to a proximal end of the guide tube. The tube includes a first curved portion having a predetermined curvature in a vicinity of the curved location and configured to enable formation of a clearance between the insert object and the tube when the distal end of the insert object has been inserted to the opening. A second curved portion having a curvature greater than the predetermined curvature so that the channel has a diameter greater than the opening. The restrictor is configured to be switchable between a first situation in which the restrictor is disposed extending along the first curved portion. A second situation in which the restrictor presses the insert object against an inner wall surface of the guide tube so that the insert object extends along and in parallel to the second curved portion.

A further aspect of the disclosed technology is directed to a method of operating an insertion assist system for an endoscope into an affected part, the method comprises directing an insertion portion of the endoscope to advance along a guide surface of a tube configured to control movement of the insertion portion during an advancing direction, restricting a path along which the insertion portion advances, by moving a restrictor, which is disposed facing the guide surface in a direction toward the guide surface and pressing the restrictor against the insertion portion, and resulting the endoscope to advance with the path remaining restricted, whereby the endoscope is caused to protrude in a predetermined direction from an opening of the tube.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. An insertion assist system comprising:
a tube configured to control a movement of an insertion portion of an endoscope through the tube, wherein the tube comprises:
an opening configured to receive the insertion portion to protrude therefrom, and
a guide surface configured to guide the insertion portion to protrude in a protruding direction from the opening, and
a restrictor disposed inside the tube and configured to adjust the protruding direction of the insertion portion from the opening, the restrictor having a surface facing the guide surface and the restrictor being configured to move the surface in an advancing direction of the insertion portion to move the insertion portion in the advancing direction toward the guide surface, and
a manipulator connected to an end of the tube,
wherein the manipulator comprises a first manipulator and a second manipulator;
the first manipulator being configured to advance and retract the insertion portion in the tube and to cause the insertion portion to protrude from the opening at an opposite end of the tube, and
the second manipulator being configured to move the surface of the restrictor toward the guide surface.

2. The insertion assist system of claim 1, wherein the restrictor:
having a band shape,
being flexible so as to conform to a shape of the guide surface,
having one end attached to the opening of the tube and having an opposite end connected to the second manipulator, and
being configured to be moved toward a clearance in the tube by an operation of the second manipulator so that the insertion portion moves toward the guide surface.

3. The insertion assist system of claim 1, wherein the restrictor:
having a band shape,
being flexible so as to conform to a shape of the guide surface,
is attached to the tube so as to form a water tight cavity with the tube, and
is configured to move by expansion toward a clearance in the tube so that the insertion portion moves toward the guide surface when a fluid is injected in the cavity.

4. The insertion assist system of claim 1, wherein:
the restrictor formed as a rigid member having a distal end portion with a curved shape that conforms to a curved portion of the guide surface,
the restrictor having a proximal end connected to the second manipulator, and
the restrictor being configured to move toward a clearance in the tube by an operation of the second manipulator so that the distal end portion of the rigid member is pressed against the insertion portion and the insertion portion moves toward the guide surface.

5. The insertion assist system of claim 1, wherein the insertion portion is configured as one of a flexible endoscope for paranasal sinus, a catheter and a guide wire.

6. The insertion assist system of claim 1, wherein the tube has a first portion extending in the advancing direction and a second portion extending in the protruding direction, the protruding direction intersecting with the advancing direction and the tube being tapered in the second portion toward the opening.

7. The insertion assist system of claim 1, wherein:
there is a clearance between the guide surface having a predetermined curvature and the insertion portion of the endoscope when the distal end of the insertion portion of the endoscope has been inserted to the opening, and
the tube having a curved surface having a curvature less than the predetermined curvature, wherein a diameter of the tube between the guide surface and the curved surface is greater than a diameter of the opening.

8. The insertion assist system of claim 7, wherein the guide surface is disposed at an end of a portion of the tube that extends in the advancing direction.

9. The insertion assist system of claim 7, wherein the restrictor is configured to be movable between:
a first position in which the restrictor is disposed extending along the curved surface, and
a second position in which the restrictor moves the surface to move the insertion section toward the guide surface.

10. The insertion assist system of claim 1, wherein the advancing direction is a longitudinal direction of the tube, and the protruding direction intersects with the longitudinal direction of the tube.

11. The insertion assist system of claim 1,
wherein the tube comprising a portion extending in the advancing direction, the portion being disposed between the manipulator and guide surface, and
the advancing direction is a longitudinal direction of the portion, and the protruding direction intersects with the longitudinal direction.

12. The insertion assist system of claim 1, wherein the restrictor is configured to move the surface in the advancing direction to move the insertion portion against the guide surface.

* * * * *